US009713804B2

(12) United States Patent
Laha et al.

(10) Patent No.: US 9,713,804 B2
(45) Date of Patent: Jul. 25, 2017

(54) CATALYST COMPOSITION FOR THE DEHYDROGENATION OF ALKANES

(71) Applicant: SAUDI BASIC INDUSTRIES CORPORATION, Riyadh (SA)

(72) Inventors: Subhash Chandra Laha, Gujarat (IN); Antonisamy Selvanathan, Gujarat (IN); Sandeep Negi, Gujarat (IN)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 298 days.

(21) Appl. No.: 14/008,729

(22) PCT Filed: Sep. 27, 2013

(86) PCT No.: PCT/IB2013/058950
§ 371 (c)(1),
(2) Date: Sep. 30, 2013

(87) PCT Pub. No.: WO2014/049569
PCT Pub. Date: Apr. 3, 2014

(65) Prior Publication Data
US 2014/0296605 A1 Oct. 2, 2014

(30) Foreign Application Priority Data
Sep. 27, 2012 (EP) .................................... 12006766

(51) Int. Cl.
*B01J 23/06* (2006.01)
*B01J 37/03* (2006.01)
*B01J 23/00* (2006.01)
*C07C 5/333* (2006.01)
*C07C 5/32* (2006.01)

(52) U.S. Cl.
CPC ............. *B01J 23/06* (2013.01); *B01J 23/005* (2013.01); *B01J 37/03* (2013.01); *C07C 5/322* (2013.01); *C07C 5/3332* (2013.01); *C07C 2521/12* (2013.01); *C07C 2523/06* (2013.01)

(58) Field of Classification Search
CPC .......... B01J 23/005; B01J 23/06; B01J 37/03; C07C 5/322; C07C 5/3332
See application file for complete search history.

(56) References Cited

U.S. PATENT DOCUMENTS 4,962,266 A 10/1990 Shum
5,073,662 A * 12/1991 Olbrich .................... B01J 23/60 585/654
5,414,182 A 5/1995 Iezzi et al.
5,430,220 A 7/1995 Khare et al.
5,877,369 A 3/1999 Wu et al.
6,017,844 A * 1/2000 Wu ........................ C10G 45/62 502/208
6,797,850 B2 9/2004 Kourtakis et al.
7,279,611 B2 10/2007 Alerasool et al.
2011/0144400 A1 6/2011 Mian et al.

FOREIGN PATENT DOCUMENTS

CN 1304873 7/2001
EP 0557982 B1 1/1997
EP 0937697 B1 6/2003

OTHER PUBLICATIONS

Extended European Search Report; European Application No. 12006766.5; Date of Mailing: Mar. 11, 2013; 6 Pages.
International Search Report for PCT/IB2013/058950 mailed Feb. 18, 2014, 4 pages.
Written Opinion of the International Searching Authority for PCT/IB2013/058950 mailed Feb. 18, 2014, 5 pages.
Horvath; "Dehydrogenation—Heterogeneous"; Encyclopedia of Catalysis; vol. 3; 2003; 33 Pages.
Chinese Patent No. CN1304873; Date of Publication: Jul. 25, 2001; Machine Translation; 8 Pages.

* cited by examiner

*Primary Examiner* — Jun Li
(74) *Attorney, Agent, or Firm* — Cantor Colburn LLP

(57) ABSTRACT

The invention relates to a catalyst composition suitable for the non-oxidative dehydrogenation of alkanes having 2-8 carbon atoms comprising silico-zinc aluminate, wherein the relative molar ratios of the elements comprised in said composition are represented by $Si_xZn_{1-x}Al_2O_4$, wherein x stands for a number in the range from 0.003 to 0.76. The invention also relates to a process for the preparation of said catalyst composition, to a process for the non-oxidative dehydrogenation of alkanes, preferably isobutane using said catalyst and to the use of said catalyst in a process for the non-oxidative dehydrogenation of alkanes.

19 Claims, No Drawings

CATALYST COMPOSITION FOR THE DEHYDROGENATION OF ALKANES

CROSS REFERENCE TO RELATED APPLICATIONS

This application is a 371 of International Application No. PCT/IB2013/058950 filed Sep. 27, 2013, which claims priority to European Application No. 12006766.5, filed Sep. 27, 2012, both of which are hereby incorporated by reference in their entirety.

The invention relates to a catalyst composition suitable for the dehydrogenation of alkanes having 2-8 carbon atoms. The invention also relates to a process for the preparation of said catalyst composition and to the use of said catalyst composition in the dehydrogenation of alkanes having 2-8 carbon atoms.

Olefinic lower hydrocarbons such as propene, butenes and isobutene are very important intermediates in the petrochemical industry. Such olefins are primarily produced as co-products in catalytic and steam cracking processes. Alternatively, lower olefins can be commercially produced by catalytic dehydrogenation of the corresponding lower alkanes. An olefinic lower hydrocarbon that is of special interest is isobutene. Isobutene is produced by the dehydrogenation of isobutane and may be used as a feed stock in the manufacture of methyl-tert-butyl-ether (MTBE) as well as in the production of polymers like butylrubber, polybutene and isoprene. MTBE is made from isobutene and methanol.

Many of the known processes for dehydrogenation of alkanes make use of a chromium catalyst. For example, U.S. Pat. No. 6,797,850 discloses the use of a chromium catalyst in dehydrogenation and dehydrocyclization processes. For example, U.S. Pat. No. 7,279,611 discloses a dehydrogenation catalyst composite containing alumina, chromium oxide, lithium oxide, and sodium oxide.

However, disposal of such chromium catalyst poses problems due to environmental regulations and involves major expenditure, because chromium is a known carcinogen. Chromium exists in two stable oxidation states, namely +3 and +6. In general, chromium (VI) is more toxic than chromium (III). Long-term exposure to chromium has been associated with lung cancer in workers exposed to levels in air that were 100 to 1,000 times higher than those found in the natural environment. One of the safe methods of disposal is to reclaim Cr from the spent catalyst for reuse and then dispose the catalyst. But reclaiming Cr from the spent catalyst is not industrially feasible. Some of the other ways to use and/or dispose the spent catalyst or the waste could be to make use of it in cement bricks, in steel industry or in refractory industry.

Since chromium is undesired from a health and environmental point of view, reclaiming of Cr is not industrially feasible, non-chromium dehydrogenation catalysts are developed.

U.S. Pat. No. 5,430,220 discloses a process for preparing a dehydrogenation catalyst of the type in which a support comprising zinc aluminate is impregnated with at least one of platinum and tin from an impregnation solution, the improvement comprises simultaneous impregnating the support with the platinum and the tin by contacting the support with an impregnation solution which comprises, in solution, a tin compound, a platinum compound, and carboxylic acid. The thus prepared catalyst can be employed in the dehydrogenation of at least one alkane containing 2-8 carbon atoms per molecule in the presence of steam.

EP0557982B1 discloses a process for dehydrogenating at least one alkane containing 2 to 8 carbon atoms to at least one alkene in the presence of steam and a catalyst composition comprising zinc aluminate, at least one tin oxide and platinum, wherein said zinc aluminate has been prepared by a preparation method comprising calcining alumina and zinc oxide, characterized by employing at least one hydrated alumina in said preparation method, wherein said hydrated alumina is selected from boehmite, pseudoboehmite, and bayerite.

However, a major drawback of these catalyst compositions useful as alkane dehydrogenation catalysts is that they require an additional metal like platinum as part of the catalyst composition to be effective. Without such an additional active metal the conversion of alkanes is greatly reduced. In addition thereto, it is described that the feedstream of a conventional dehydrogenation catalyst further comprises steam.

EP0937697 discloses a catalyst for alkane dehydrogenation comprising platinum deposited upon a support which is a mixture of tin oxide and zirconium oxide. Although the dehydrogenation in EP0937697 may be conducted in the absence of steam, platinum is still required in the catalyst composition.

It is an object of the present invention to provide a catalyst suitable for the dehydrogenation of alkanes with improved catalytic performance. Furthermore, it is an object of the present invention to provide an alkane dehydrogenation process which does not require steam to be present in the feed.

This object is achieved by a catalyst composition suitable for the non-oxidative dehydrogenation of alkanes having 2-8 carbon atoms comprising silico-zinc aluminate (e.g., silico-zinc aluminate spinel), wherein the relative molar ratios of the elements comprised in said composition are represented by formula (1)

$$Si_xZn_{1-x}Al_2O_4 \quad (1)$$

wherein x stands for a number in the range from 0.003 to 0.76.

The catalyst composition of the invention provides a chromium-free catalyst for the dehydrogenation of alkanes having 2-8 carbon atoms per molecule and the dehydrogenation may be performed without the presence of steam. None of the known catalyst compositions so far comprise silico-zinc aluminate spinel.

For example, U.S. Pat. No. 5,414,182 discloses a process for activating a catalytic composition for paraffin dehydrogenation containing gallium, alumina, possibly silica and/or one or more alkaline or alkaline earth metals, comprises thermal activation in air followed by post-activation effected by the following stages: oxidation with air and/or oxygen or a mixture containing oxygen and inert gas, purging with inert gas, reduction with hydrogen or a mixture of hydrogen and an inert or reducing gas. The catalytic composition activated by said process contains gallium, alumina, silica and possibly one or more alkaline or alkaline earth metals, the alumina being in the δ or θ phase or in δ+θ phase or in a δ+θ+α phase. It is indicated in U.S. Pat. No. 5,414,182 that said catalyst may be used in a fluidized bed reactor for the dehydrogenation of alkanes to alkenes.

For example, WO2010/015341A1 discloses a material which is suitable as a carrier for catalysts in alkane dehydrogenations and in oxidative alkane dehydrogenations, and which is produced as an oxidic or non-oxidic ceramic foam, and which can contain the substances aluminum oxide, calcium oxide, silicon dioxide, tin oxide, zirconium oxide, calcium aluminate, zinc aluminate, silicon carbide and boron nitride in combination, and which is impregnated with one or more suitable catalytically active materials.

The catalyst composition of the invention may have a high activity (as shown by a high conversion and yield). Also, the catalyst composition of the invention may have a good selectivity towards isobutene. Furthermore, this high activity and/or selectivity may even be present in the absence of steam in the feed. Furthermore, the catalyst may have improved stability; that is it may maintain its activity for longer periods of use and/or more catalyst regeneration cycles.

As such, the catalyst composition of the invention not only provides an environmentally benign alternative to chromium catalysts, but also an improved catalyst composition for the non-oxidative dehydrogenation of alkanes having 2 to 8 C-atoms per molecule.

As used herein, the term "catalyst composition" is understood to mean a composition consisting of the catalyst (active phase) and any other suitable components. The catalyst composition of the invention is for example suitable for the non-oxidative dehydrogenation of an alkane and for example particularly suitable for the non-oxidative dehydrogenation of isobutane.

As used herein, the term "non-oxidative dehydrogenation" is understood to mean that the dehydrogenation proceeds substantially in the absence of an oxidizing agent such as oxygen or steam, i.e. the amount of the oxidizing agent in the feed stream is at most 5 vol %, for example at most 1 vol %, more preferably does not substantially contain an oxidizing agent.

Preferably, said alkene is selected from the group consisting of ethylene, propylene, n-butene, isobutene, 1,3-butadiene and mixtures thereof and said alkane is selected from the group consisting of ethane, propane, n-butane, isobutane, and mixtures thereof. Most preferably, the process according to the invention is a process for producing isobutene from isobutane.

With silico-zinc aluminate is meant $Si_xZn_{1-x}Al_2O_4$. Its presence can be confirmed using X-ray diffraction (XRD). For purpose of this invention, the X-ray source for XRD is operated at 40 kV and 30 mA and is scanned at a rate of 0.05 deg/min from a 2θ value of 5° to 70°.

Next to silico-zinc aluminate, the composition of the present invention may also comprise zinc aluminate and/or oxides of silicon, zinc and/or aluminum. Therefore, the invention also relates to a catalyst composition further comprising zinc aluminate and/or an oxide of silicon and/or an oxide of aluminum and/or an oxide of zinc. The zinc aluminate may have a spinel structure.

The relative molar ratios of the elements comprised in the composition of the invention is represented by formula (1)

$$Si_xZn_{1-x}Al_2O_4 \quad (1)$$

In formula (1(, x stands for a number in the range from 0.003 to 0.76.

For example x is at least 0.005, for example at least 0.01, for example at least 0.05 and/or at most 0.6, for example at most 0.5. For example, x is in the range from 0.03 to 0.15.

Preferably, the catalyst composition of the invention is essentially platinum free.

As used herein, the term "essentially free" when related to a certain (group of) element(s), preferably platinum, means to describe a catalyst composition wherein the comprised amount of said (group of) element(s) is too low to have an effect on catalyst performance. In one embodiment, the catalyst composition of the invention comprises less than 0.05 wt-% of said (group of) element(s), preferably less than 0.01 wt-% of said (group of) element(s), more preferably less than 0.005 wt-% said (group of) element(s) and even more preferably less than 0.001 wt-%. Particularly preferably, the content of said certain (group of) element(s) is below the detection limit of e.g. 60 ppm for platinum, when using Atomic Adsorption Spectroscopy. Most preferably, the catalyst composition comprises no platinum. In one embodiment, the catalyst composition is essentially free from one or more elements selected from Group 10 of the Periodic Table (IUPAC version of 22 Jun. 2007).

The silico-zinc aluminate and/or the zinc aluminate may have spinel structure. The term "spinet structure" is well known in the art and is defined herein as an aluminum comprising mixed oxide having the general formulation $Z^{2+}Al_2^{3+}O_4^{2-}$ which is crystallised in the cubic (isometric) crystal system and wherein the oxide anions are arranged in a cubic close-packed lattice and wherein the cations "Z" and Al occupy some or all of the octahedral and tetrahedral sites in the lattice.

Preferably, the invention relates to a catalyst composition of the invention, wherein the silico-zinc aluminate has a spinel structure.

Preferably, the invention relates to a catalyst composition according to the invention, wherein the catalyst composition additionally comprises M, wherein M is selected from the group of alkali, alkaline earth metals, 3-5 d elements and mixtures thereof, wherein the relative molar ratios of the elements comprised in said composition are represented by formula (1a)

$$M/Si_xZn_{1-x}Al_2O_4 \quad (1a)$$

wherein x is as defined herein.

When M is present in the catalyst composition of the invention, M is selected from the group of alkali, alkaline earth metals, 3-5 d elements and mixtures comprising at least one of the foregoing. Preferably, M is selected from the group of sodium (Na), potassium (K), cesium (Cs), rubidium (Rb), strontium (Sr), barium (Ba), magnesium (Mg), calcium (Ca), gallium (Ga), germanium (Ge), tin (Sn), copper (Cu), zirconium (Zr), cobalt (Co), manganese (Mn), molybdenum (Mo), tungsten (W), and mixtures comprising at least one of the foregoing.

M may for example be present in an amount from 0.01 to 5.0 wt %, preferably 0.01 to 1.5 wt %, for example 0.01-0.1 wt % based on the silico-zinc aluminate.

For example, M may be present in an amount of at least 0.02, for example at least 0.03, for example at least 0.04, for example at least 0.05, for example at least 0.1, for example at least 0.2, for example at least 0.3 and/or for example at most 1.4, for example at most 1.3, for example at most 1.2, for example at most 1.1, for example at most 1.0 wt % based on the silico-zinc aluminate present in the catalyst composition. For example M may be present in an amount of from 0.05 to 1.2 wt % based on the silico-zinc aluminate present in the catalyst composition.

In another aspect, the invention relates to a process for the preparation of a catalyst composition according to the invention comprising the steps of:

(a) preparing a solution and/or suspension comprising silicon, zinc and aluminum to form a silicon- and zinc- and aluminum-comprising solution and/or suspension, (b) admixing a basic solution, preferably ammonia, to the silicon- and zinc- and aluminum-comprising solution and/or suspension to co-precipitate mixed hydroxides and/or oxides of zinc, aluminum and silicon, and (c) calcining the co-precipitate formed in step b) to obtain silico-zinc aluminate.

The solution and/or suspension may comprise silicon in the form of a salt, silicate, oxide, silica gel and/or silicic acid. Zinc and aluminum are preferably present in the solution and/or suspension in the form of a salt.

The solution and/or suspension comprising silicon, zinc and aluminum may for example be prepared by (a1) preparing a solution and/or suspension of silicon, wherein silicon is in the form of a salt, silicate, oxide, silica gel and/or silicic acid (a2) preparing a solution of zinc comprising salts and aluminum comprising salts and (a3) mixing the solution and/or suspension of silicon with the solution of zinc comprising salts and aluminum comprising salts to form the solution and/or suspension comprising silicon, zinc and aluminum.

The solution and/or suspension may be made in any suitable solvent, preferably water, most preferably demineralised water. Suitable solvents are all liquid compounds in which the zinc and aluminum salts are soluble and which are easy to remove/separate when the solid co-precipitate is formed. The solutions and/or suspensions of step (a1) and/or step (a3) and/or of the solution of step (a2) may be heated to at least 60° C. and up to 95° C. (60-95° C.), most preferably to 75-85° C. to facilitate the solvation of the zinc- and aluminum comprising salts. The preferred solvent is water, most preferably demineralised water.

Any salts of zinc and aluminum that are soluble in the selected solvent may be used to prepare the zinc- and aluminum-comprising solution or the silicon, zinc and aluminum comprising solution and/or suspension. Suitable zinc-, and aluminum-sources may be used in the form of nitrate, chloride, carbonate, and bicarbonate. A particularly suitable soluble zinc salt is zinc nitrate hexahydrate, a particularly suitable soluble aluminum salt is aluminum nitrate nonahydrate.

Preferably as a basic solution in step b, ammonia is used.

In the precipitation step (b) a basic solution, preferably ammonia, for example a solution of 5 to 30 wt % ammonia in water, is admixed to the silicon, zinc and aluminum comprising solution and/or suspension to form (amongst others) a co-precipitate of mixed hydroxides and/or oxides of silicon, zinc and aluminum, preferably under constant agitation. Other suitable bases include, but are not limited to sodium carbonate ($Na_2CO_3$), $K_2CO_3$, $(NH_4)_2CO_3$ and $NH_4OH$. Preferably, the base is added in a controlled fashion until the pH of the mixture reaches a value of 7.0 to 8.0. The temperature during the precipitation step may be kept at 60-95° C., preferably at 75-85° C. After adding the base the obtained mixture is preferably kept at elevated temperature under constant agitation for 0.5-5 hours.

After step (b) and before step (c) as described herein, the co-precipitate is preferably separated from the liquid (i.e. the liquid phase of the mixture that is formed after completing the precipitate forming step (b)) using any conventional method which allows the separation of a precipitate from a liquid. Suitable methods include, but are not limited to, filtering, decanting and centrifugation. Subsequently the obtained solid may be washed, preferably using one of the solvents in which the solution(s) and/or suspension(s) was/were made, more preferably with water, most preferably with demineralised or distilled water. The solid then may be dried, preferably at 90-120° C. for 2-16 hours.

Finally, in the calcination step (c), the calcination of the co-precipitate prepared in step b is performed by calcining the co-precipitate by heating the obtained co-precipitate in an oxygen containing atmosphere to form silico-zinc aluminate. Preferably, said calcination is performed at a temperature of 500 to 1100° C., more preferably at a temperature of 600 to 900° C., most preferably at a temperature of 700 to 800° C. for two to 24 hours in an oxygen containing environment, preferably air.

A catalyst composition prepared using a calcination temperature of 600 to 900° C. may be more active and selective and more stable than plain zinc aluminate catalysts in the same non-oxidative dehydrogenation process.

Preferably, the catalyst composition as defined herein is prepared with the process for the preparation of a catalyst composition of the present invention.

After step (c), but prior to use, the catalyst composition may be contacted with a reducing agent. Preferably the said reducing agent is selected from the group consisting of hydrogen ($H_2$) and hydrocarbons having 2 to 5 carbon atoms. Therefore, the invention also relates to a process for the preparation of a catalyst composition according to the invention further comprising the step of (d) contacting the catalyst composition obtained in step (c) with a reducing agent, preferably wherein the reducing agent is selected from the group of hydrogen ($H_2$) and hydrocarbons having 2 to 5 carbon atoms per molecule.

Optionally, in the process of the invention, the silicon- and zinc- and aluminum-comprising solution and/or suspension further comprises M before admixing the basic solution in step (b), or wherein the silico-zinc aluminate formed in step (c) is contacted with an M-comprising salt solution, wherein M is as defined above.

For the avoidance of doubt, with an 'M-comprising salt' is meant a salt of M, wherein M is selected from the group of sodium (Na), potassium (K), cesium (Cs), rubidium (Rb), strontium (Sr), barium (Ba), magnesium (Mg), calcium (Ca), gallium (Ga), germanium (Ge), tin (Sn), copper (Cu), zirconium (Zr), cobalt (Co), manganese (Mn), molybdenum (Mo), tungsten (W) and mixtures comprising at least one of the foregoing.

Similarly, with zinc comprising salt, or aluminum comprising salt is meant a salt of zinc or a salt of aluminum, respectively.

Any M that is soluble in the selected solvent may be used to modify the silico-zinc aluminate. Salts may be in the form of acetate, oxalate, nitrate, chloride, carbonate, and bicarbonate. For example, a particularly suitable soluble tin salt is tin chloride and a particularly suitable soluble gallium salt is gallium nitrate.

Any salt of zinc or aluminum that is soluble in the selected solvent may be used. For example, suitable salts may be used in the form of nitrate, chloride, carbonate and bicarbonate.

Preferably, one or more of the salts in the silicon- and zinc- and aluminum-comprising solution and/or suspension or at least one of the salts in the M-comprising salt solution or the silicon- and zinc- and aluminum solution and/or suspension further comprising M or in the M-comprising salt solution is a nitrate salt. Preferably all salts in the silicon- and zinc- and aluminum-comprising solution and/or suspension and/or in the M-comprising salt solution are nitrate salts.

The catalyst composition of the present invention is preferably formed in regularly sized particles such as conventionally formed catalyst pellets and/or sieved catalyst particles. The catalyst composition of the present invention may comprise further components such as diluents. Any inert catalyst diluent may be used, for example in a 1:4 to 4:1, for example in a 1:2 to 2:1 weight ratio, for example in a weight ratio of around 1:1 diluent to silico-zinc aluminate. Preferably, the diluent is alpha alumina.

The catalyst composition of the invention can be readily distinguished from known catalysts (which do not contain silico-zinc aluminate) by known methods such as by X-ray diffraction (XRD). For purpose of this invention, the X-ray source for XRD is operated at 40 kV and 30 mA and is scanned at a rate of 0.05 deg/min from a 2θ value of 5° to 70°.

In another aspect, the invention relates to a catalyst composition obtained or obtainable by the process of the invention.

In another aspect, the invention relates to a process for the non-oxidative dehydrogenation of alkanes having 2-8 carbon atoms, preferably isobutane, comprising the step of contacting said alkanes with the catalyst composition of the invention.

In another aspect, the invention relates to a process for producing an alkene by non-oxidative dehydrogenation of an alkane comprising the step of contacting a feed stream comprising the alkane with the catalyst composition of the invention to form the alkene.

In the framework of the invention, with alkane is meant a hydrocarbon with general formula $C_nH_{2n+2}$. For example, the alkane can have from 2 to 12, preferably from 2 to 4 carbon atoms per molecule. For example, the alkane may be propane, butane, pentane, hexane, heptane, octane, nonane, decane, or a mixture comprising at least one of the foregoing. Preferably, the alkane is propane.

Examples of alkenes that may be produced in the process of the invention include but are not limited to propene (also referred to herein as propylene) and ethylene (also referred to herein as ethene) and butene.

The alkane may be used in its pure form, but may also be present in a feed-stream of a mixture of alkanes or in a feed-stream of alkane (also referred to herein as alkane feed-stream) with an inert gas, such as $N_2$. Preferably, the alkane is present in a feed-stream that predominantly comprises one alkane species.

Accordingly, it is preferred that the alkane comprised in the feed-stream consists of at least 75 mol % of only one alkane species, more preferably of at least 85 mol % of only one alkane species, even more preferably of at least 90 mol % of only one alkane species, particularly preferably of at least 95 mol % of only one alkane species and most preferably of at least 98 mol % of only one alkane species.

Preferably, the total amount of alkane in the feed-stream is at least 98 wt %, preferably at least 99 wt %, for example at least 99.5 wt %, for example at least 99.7 wt %, for example 99.9 wt % based on the total feed-stream. Accordingly, the process is performed with little or no amount of feed diluents. This has an advantage of eliminating a downstream diluents separation step which leads to the reduction of overall operation cost. The throughput for a given size of reactor is increased.

Small amounts of olefins (for example from 0.1 to 0.5 wt % based on the total feed-stream) may be present in the feed-stream.

The feed-stream may also comprise hydrogen. For example, the molar ratio of hydrogen to alkane in the feed-stream may be in the range from about 1:6 to 0:1.

The feed-stream may also comprise an inert gas diluent. The inert gas diluent may be chosen from the group of helium, nitrogen, and mixtures comprising at least one of the foregoing, preferably nitrogen. For example, the molar ratio of alkane to inert gas diluent may be in the range from about 1:10 to about 1:1.

It is evident for the skilled person that the process of the present invention is performed under non-oxidative dehydrogenation conditions. Process conditions useful in the process of the present invention, also described herein as "alkane dehydrogenation conditions", can be easily determined by the person skilled in the art; see Horvath (2003) Encyclopaedia of Catalysis Volume 3, 49-79, Preferably, the process for the non-oxidative dehydrogenation of alkanes of the invention is performed at a reaction temperature of 500-600° C., a weight hourly space velocity (WHSV) of 0.1-1 $h^{-1}$ and a pressure of 0.01-0.3 MPa.

The step of contacting the feed stream comprising the alkane with the catalyst composition of the invention may for example be performed in a reactor at a temperature from 500 to 650° C. Preferably, the step of contacting the feed stream comprising the alkane with the catalyst composition of the invention is performed at a temperature of from 400 to 650, preferably at a temperature from 500 to 600° C. A lower temperature has the advantage that the energy required for the non-oxidative dehydrogenation is also lower.

The pressure within the reactor in which the non/oxidative dehydrogenation is performed is 0.01-0.3 MPa, for example around atmospheric pressure (1 atmosphere).

The weight hourly space velocity (WHSV), that is the ratio of the weight of the alkane which comes in contact with a given weight of catalyst per unit time, is for example in the range from 0.1 to 10 $hour^{-1}$, for example the weight hourly space velocity is 0.1 to 1 $hour^{-1}$.

The step of contacting the alkane with the catalyst composition of the invention may be performed in any suitable reactor, as known to a skilled person, for example in a fixed bed or moving bed reactor. The alkane having 2-8 carbon atoms is preferably isobutane.

Accordingly, a process for dehydrogenating alkanes having 2-8 carbon atoms is provided comprising the steps of (a) preparing a solution and/or suspension comprising silicon, zinc and aluminum to form a silicon- and zinc- and aluminum-comprising solution and/or suspension, (b) admixing a basic solution, preferably ammonia, to the silicon- and zinc- and aluminum-comprising solution and/or suspension to form a co-precipitate of hydroxides and/or oxides of zinc, aluminum and silicon, (c) calcining the co-precipitate formed in step b) to obtain silico-zinc aluminate, and (d) contacting the silico-zinc aluminate with said alkanes under alkane dehydrogenation conditions.

In another aspect, the invention relates to use of the catalyst composition of the invention in the non-oxidative dehydrogenation of an alkane.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will now be elucidated by way of the following examples without however being limited thereto.

EXAMPLES

Example 1

Preparation of Silico-Zinc Aluminate 27.63 g zinc nitrate hexahydrate was dissolved in 60 ml demineralised water. 69.68 g of aluminum nitrate nonahydrate was dissolved in 230 ml of demineralised (DM) water. 1.0 g silica gel was mixed in 20 ml of DM water. All three solutions/mixtures were mixed in a four-necked round bottom flask (1000 ml) equipped with dropping funnel, reflux condenser and thermometer. The mixture was slowly heated to 80° C. Then aqueous ammonia solution (10 wt %) was added drop wise to the mixture with continuous stilling. The addition was stopped when the pH of the hot mixture in the 4-neck flask was measured 7.0-8.0. This mixture was further digested at 80° C. for 2 hours. Then the hot slurry formed was filtered under vacuum and washed with DM water up to the pH of the filtrate was reached 7.0. Then the wet cake was dried at 100° C. in an air oven for 4 hours. The dried solid was, then, calcined in a muffle furnace at 800° C. for 4 hours in presence of air.

Example 2

Preparation of Catalyst Particles

A number of catalyst compositions comprising different silico-zinc aluminates and binder or diluents (alpha alumina) were prepared in particle form by mixing the silico-zinc aluminate and the binder support thoroughly in a 1:1 weight ratio. The mixture was pressed at 10 ton pressure to make pellets. The pressed catalyst compositions were crushed and sieved. The fraction containing particles from 0.5 to 1.0 mm were selected for further use. The particles of the active silico-zinc aluminate component, and binder were also prepared separately after which the two components (in particle forms) were mixed in a 1:1 ratio (wt/wt) to prepare the final catalyst composition and perform the catalytic testing.

Example 3

Catalyst Testing

Five grams catalyst particles (particle size 0.5-1.0 mm) were loaded in a down flow fixed bed micro catalytic reactor and pre-treated in the following way:

Step 1: Exposed for 10-60 min to nitrogen at the flow rate of 100 ml/min at 550° C.

Step 2: Exposed for 5-60 min to hydrogen at the flow rate of 100 ml/min at 550° C.

After the pre-treatment, isobutane was fed to the reactor at 19 ml/min. The temperature of the catalyst bed before start of isobutane flow was maintained at 550° C. Pure isobutane was used as feed-stream. The Weight Hourly Space Velocity (WHSV) was 0.54 $h^{-1}$. The product stream coming out of the reactor was analyzed by an on-line Gas Chromatograph with a plot $Al_2O_3/Na_2SO_4$ column using a Flame Ionization Detector (FID).

After the reaction, the catalyst was regenerated in the following way:

Step 1: Exposed for 10 min to air at the flow rate of 100 ml/min at 550-560° C.

Step 2: Exposed for 10 min to nitrogen at the flow rate of 100 ml/min at 550-560° C.

Step 3: Exposed for 5 min to hydrogen at the flow rate of 100 ml/min at 550-560° C.

After the regeneration of the catalyst, isobutane was fed to the bed at 19 ml/min and the dehydrogenation reaction was continued.

Results

Table 1 provides the catalytic performance (isobutane conversion and isobutene selectivity) study for isobutane dehydrogenation (Reaction temperature=550° C., Pressure=1 atmosphere, WHSV=0.54 $h^{-1}$). Reactions were conducted for 8 min. The catalyst used was silico-zinc aluminate (prepared using 1 wt % of silica or equivalent molar amount of different silica sources); alpha-alumina was taken as diluent/binder. Active component to binder ratio was considered as 1:1 (wt/wt) for the final catalyst composition.

Table 2 provides the catalytic performance (isobutane conversion and isobutene selectivity) study of many cycles and catalyst's stability for isobutane dehydrogenation (Reaction temperature=550° C., Pressure=1 atmosphere, WHSV=0.54 $h^{-1}$). Reaction was conducted for 8 min and then the catalyst was regenerated. The catalyst used was silico-zinc aluminate (prepared using 5 wt % of silica gel); alpha-alumina was taken as diluent/binder. Active component to binder ratio was considered as 1:1 (wt/wt) for the final catalyst composition.

Table 3 provides the catalytic performance (isobutane conversion and isobutene selectivity) study for different catalyst batches for isobutane dehydrogenation (Reaction temperature=550° C., Pressure=1 atmosphere, WHSV=0.54 $h^{-1}$). Reactions were conducted for 50 min. The catalyst used was silico-zinc aluminate (prepared using 5 wt % of silica gel); alpha-alumina was taken as diluent/binder. Active component to binder ratio was considered as 1:1 (wt/wt) for the final catalyst composition.

As can be seen from Table 1, catalysts of the invention showed a good isobutane conversion and isobutene selectivity for isobutane dehydrogenation reaction screened with different silico-zinc aluminate catalysts prepared using different silica sources. Moreover, catalysts of the invention show a high selectivity for isobutene (see entry 1-4 in Table 1).

As can be seen from Table 2, catalyst of the invention showed a good and reproducible isobutane conversion and high selectivity for isobutane dehydrogenation reaction for many reaction-regeneration catalytic cycles. Moreover, catalyst of the invention showed a high stability (see entry 1-6 in Table 2) up to 500 cycles. This shows that catalysts of the invention maintain their activity over long periods of time.

As can be seen from Table 3, the catalyst of the invention showed a reproducible isobutane conversion and high selectivity for isobutane dehydrogenation reaction for different catalyst synthesis batches. This shows that catalysts of the invention show reproducible catalytic performance from different catalyst batches.

TABLE 1

Table 1: Comparison of catalytic performance studies for isobutane dehydrogenation reaction using catalyst composition comprising $Si_xZn_{1-x}Al_2O_4$ (x = 0.036) + alpha-alumina (1:1) as principal components. The conversion and selectivity given in this table were collected after 8 min of reaction.

| Silica Source | Isobutane Conversion (%) | Isobutene Selectivity (%) |
|---|---|---|
| Silica gel | 51.4 | 89.0 |
| Colloidal silica | 48.3 | 97.0 |

TABLE 1-continued

Table 1: Comparison of catalytic performance studies for isobutane dehydrogenation reaction using catalyst composition comprising $Si_xZn_{1-x}Al_2O_4$ (x = 0.036) + alpha-alumina (1:1) as principal components. The conversion and selectivity given in this table were collected after 8 min of reaction.

| Silica Source | Isobutane Conversion (%) | Isobutene Selectivity (%) |
|---|---|---|
| Sodium silicate | 49.3 | 95.8 |
| Silicic acid | 54.5 | 94.2 |

TABLE 2

Table 2: Catalytic performance studies over several reaction cycles for isobutane dehydrogenation reaction using catalyst composition comprising $Si_xZn_{1-x}Al_2O_4$ (x = 0.18) + alpha-alumina (1:1) as principal components. The conversion and selectivity given in this table were collected after 8 min of reaction. The catalyst was regenerated after 8 min of reaction.

| No of Cycles | Isobutane Conversion (%) | Isobutene Selectivity (%) |
|---|---|---|
| 1 | 53.5 | 90.9 |
| 103 | 48.6 | 92.8 |
| 201 | 48.6 | 92.7 |
| 299 | 48.6 | 92.5 |
| 404 | 48.7 | 91.7 |
| 497 | 47.1 | 91.2 |

TABLE 3

Table 3: Catalytic performance studies of different catalyst batches for isobutane dehydrogenation reaction using catalyst composition comprising $Si_xZn_{1-x}Al_2O_4$ (x = 0.18) + alpha-alumina (1:1) as principal components. The conversion and selectivity given in this table were collected after 50 min of reaction.

| No of Batches | Isobutane Conversion (%) | Isobutene Selectivity (%) |
|---|---|---|
| 1 | 52.8 | 93.4 |
| 2 | 52.1 | 91.8 |
| 3 | 50.5 | 89.1 |
| 4 | 49.7 | 92.8 |
| 5 | 49.5 | 89.2 |

Set forth below are some embodiments of the catalyst and processes disclosed herein.

Embodiment 1

A catalyst composition suitable for the non-oxidative dehydrogenation of alkanes having 2-8 carbon atoms comprising silico-zinc aluminate (e.g., silico-zinc aluminate spinel), wherein the relative molar ratios of the elements comprised in said composition are represented by formula (1)

$$Si_xZn_{1-x}Al_2O_4 \quad (1)$$

wherein x stands for a number in the range from 0.003 to 0.76.

Embodiment 2

A catalyst composition suitable for the non-oxidative dehydrogenation of alkanes having 2-8 carbon atoms comprising silico-zinc aluminate (e.g., silico-zinc aluminate spinel), wherein the relative molar ratios of the elements comprised in said composition are represented by formula (1)

$$Si_xZnAl_2O_4 \quad (1)$$

wherein x stands for a number in the range from 0.003 to 0.76.

Embodiment 3

The catalyst composition according to Embodiment 1 or Embodiment 2, wherein said catalyst composition is essentially platinum free.

Embodiment 4

The catalyst composition according to any one of Embodiments 1-3, wherein the silico-zinc aluminate has a spinel structure.

Embodiment 5

The catalyst composition according to any one of Embodiments 1-4, wherein the catalyst composition additionally comprises M, wherein M is selected from the group of alkali, alkaline earth metals, 3-5 d elements and mixtures thereof, wherein the relative molar ratios of the elements comprised in said composition are represented by formula (1a)

$$M/Si_xZn_{1-x}Al_2O_4 \quad (1a)$$

wherein x is as defined above.

Embodiment 6

The catalyst composition according to Embodiment 5, wherein M is selected from the group of sodium (Na), potassium (K), cesium (Cs), rubidium (Rb), strontium (Sr), barium (Ba), magnesium (Mg), calcium (Ca), gallium (Ga), germanium (Ge), tin (Sn), copper (Cu), zirconium (Zr), cobalt (Co), manganese (Mn), molybdenum (Mo), tungsten (W) and mixtures comprising at least one of the foregoing.

Embodiment 7

The catalyst composition according to Embodiment 5 or Embodiment 6, wherein M is present in an amount from 0.01 to 5 wt % based on the silico-zinc aluminate.

Embodiment 8

The catalyst composition according to Embodiment 7, wherein M is present in an amount from 0.01 to 1.5 wt % based on the silico-zinc aluminate.

Embodiment 9

The catalyst composition according to Embodiment 8, wherein M is present in an amount from 0.01-0.1 wt % based on the silico-zinc aluminate.

Embodiment 10

The catalyst composition according to any one of Embodiments 1-9, wherein the catalyst composition further comprises zinc aluminate and/or an oxide of silicon and/or an oxide of aluminum and/or an oxide of zinc.

Embodiment 11

Process for the preparation of a catalyst composition according to any one of Embodiments 1-10 comprising:

(a) preparing a solution and/or suspension comprising silicon, zinc and aluminum to form a silicon- and zinc- and aluminum-comprising solution and/or suspension, (b) admixing a basic solution, preferably ammonia, to the silicon- and zinc- and aluminum-comprising solution and/or suspension to co-precipitate mixed hydroxides and/or oxides of zinc, aluminum and silicon, and (c) calcining the co-precipitate obtained in step (b).

Embodiment 12

The process according to Embodiment 11, wherein the silicon- and zinc- and aluminum-comprising solution and/or suspension further comprises M before admixing the basic solution in step (b).

Embodiment 13

The process according to Embodiment 11, wherein the silico-zinc aluminate formed in step (c) is contacted with an M-comprising salt solution.

Embodiment 14

The process according to any one of Embodiments 11-13, wherein one or more of the salts in the silicon- and zinc- and aluminum-comprising solution and/or suspension or at least one of the salts in the M-comprising salt solution or the silicon- and zinc- and aluminum solution and/or suspension further comprising M or in the M-comprising salt solution is a nitrate salt.

Embodiment 15

The process according to any one of Embodiments 11-14, wherein one or more of the salts in the silicon- and zinc- and aluminum-comprising solution and/or suspension is a nitrate salt.

Embodiment 16

The process according to any one of Embodiments 11-14, wherein at least one of the salts in the M-comprising salt solution is a nitrate salt.

Embodiment 17

The process according to any one of Embodiments 11-14, wherein the silicon- and zinc- and aluminum solution and/or suspension further comprising M is a nitrate salt.

Embodiment 18

The process according to any one of Embodiments 11-17, wherein the silico-zinc aluminate is calcined at 500-1100° C. for 2-24 hours in an oxygen containing atmosphere.

Embodiment 19

The process according to any one of Embodiments 11-18, wherein the silico-zinc aluminate is calcined at 600-900° C. for 2-24 hours in an oxygen containing atmosphere.

Embodiment 20

The process according to any one of Embodiments 11-19, wherein the silico-zinc aluminate is calcined at 700-800° C. for 2-24 hours in an oxygen containing atmosphere.

Embodiment 21

The process according to any one of Embodiments 18-20 wherein the oxygen containing atmosphere is air.

Embodiment 22

The process according to any one of Embodiments 11-21, further comprising (d) contacting the catalyst composition obtained in step (c) with a reducing agent.

Embodiment 23

The process according to Embodiment 22, wherein the reducing agent is selected from the group of hydrogen ($H_2$) and hydrocarbons having 2 to 5 carbon atoms per molecule.

Embodiment 24

The catalyst composition obtained or obtainable by the process of any one of Embodiments 11-23.

Embodiment 25

The process for the non-oxidative dehydrogenation of alkanes having 2-8 carbon atoms, preferably isobutane, comprising the step of contacting said alkanes with the catalyst composition of any one of Embodiments 1-10 or 24.

Embodiment 26

The process according to Embodiment 25, wherein the alkane comprises isobutane.

Embodiment 27

The process according to any one of Embodiments 25-26, wherein the process is performed at a reaction temperature of 500-600° C., a weight hourly space velocity (WHSV) of 0.1-1 $h^{-1}$ and a pressure of 0.01-0.3 MPa.

We claim:

1. A catalyst composition suitable for the non-oxidative dehydrogenation of alkanes having 2-8 carbon atoms comprising silico-zinc aluminate, wherein the relative molar ratios of the elements comprised in said composition are represented by formula (1)

$$Si_xZn_{1-x}Al_2O_4 \quad (1)$$

wherein x stands for a number in the range from 0.05 to 0.76.

2. The catalyst composition according to claim 1, wherein the catalyst composition further comprises zinc aluminate and/or an oxide of silicon and/or an oxide of aluminum and/or an oxide of zinc.

3. The catalyst composition according to claim 1, wherein said catalyst composition is essentially platinum free.

4. The catalyst composition according to claim 1, wherein the silico-zinc aluminate has a spinel structure.

5. The catalyst composition according to claim 1, wherein the catalyst composition additionally comprises M, wherein M is selected from the group of alkali, alkaline earth metals, 3-5d elements and mixtures thereof, wherein the relative molar ratios of the elements comprised in said composition are represented by formula (1a)

$$M/Si_xZn_{1-x}Al_2O_4 \quad (1a)$$

wherein x is as defined above.

6. The catalyst composition according to claim 5, wherein M is selected from the group of sodium (Na), potassium (K), cesium (Cs), rubidium (Rb), strontium (Sr), barium (Ba), magnesium (Mg), calcium (Ca), gallium (Ga), germanium (Ge), tin (Sn), copper (Cu), zirconium (Zr), cobalt (Co), manganese (Mn), molybdenum (Mo), tungsten (W) and mixtures comprising at least one of the foregoing.

7. The catalyst composition according to claim 5, wherein M is present in an amount from 0.01 to 5 wt % based on the silico-zinc aluminate.

8. Process for the preparation of a catalyst composition according to claim 1 comprising:

(a) preparing a solution and/or suspension comprising silicon, zinc and aluminum to form a silicon- and zinc- and aluminum-comprising solution and/or suspension, (b) admixing a basic solution, preferably ammonia, to the silicon- and zinc- and aluminum-comprising solution and/or suspension to co-precipitate mixed hydroxides and/or oxides of zinc, aluminum and silicon, and (c) calcining the co-precipitate obtained in step (b).

9. The process according to claim 8, wherein the silicon- and zinc- and aluminum-comprising solution and/or suspension further comprises M before admixing the basic solution in step (b), or wherein the silico-zinc aluminate formed in step (c) is contacted with an M-comprising salt solution, wherein M is as defined above.

10. The process according to claim 8 wherein one or more of the salts in the silicon- and zinc- and aluminum-comprising solution and/or suspension or at least one of the salts in the M-comprising salt solution or the silicon- and zinc- and aluminum solution and/or suspension further comprising M or in the M-comprising salt solution is a nitrate salt.

11. The process according to claim 8, wherein the silico-zinc aluminate is calcined at 500-1100° C. for 2-24 hours in an oxygen containing atmosphere.

12. The process according to claim 8, further comprising (d) contacting the catalyst composition obtained in step (c) with a reducing agent.

13. The process for the non-oxidative dehydrogenation of alkanes having 2-8 carbon atoms comprising contacting said alkanes with the catalyst composition of claim 1.

14. The process according to claim 13, wherein the process is performed at a reaction temperature of 500-600° C., a weight hourly space velocity (WHSV) of 0.1-1 $h^{-1}$ and a pressure of 0.01-0.3 MPa.

15. A catalyst composition suitable for the non-oxidative dehydrogenation of alkanes having 2-8 carbon atoms comprising silico-zinc aluminate, wherein the relative molar ratios of the elements comprised in said composition are represented by formula (1)

$$Si_xZn_{1-x}Al_2O_4 \quad (1)$$

wherein x stands for a number in the range from 0.05 to 0.76;

wherein said catalyst composition is essentially platinum free; and wherein the silico-zinc aluminate has a spinel structure.

16. The catalyst composition according to claim 15, wherein the catalyst composition additionally comprises M, wherein M is selected from the group of alkali, alkaline earth metals, 3-5d elements and mixtures thereof, wherein the relative molar ratios of the elements comprised in said composition are represented by formula (1a)

$$M/Si_xZn_{1-x}Al_2O_4 \quad (1a)$$

wherein x is as defined above.

17. The catalyst composition according to claim 16, wherein M is selected from the group of sodium (Na), potassium (K), cesium (Cs), rubidium (Rb), strontium (Sr), barium (Ba), magnesium (Mg), calcium (Ca), gallium (Ga), germanium (Ge), tin (Sn), copper (Cu), zirconium (Zr), cobalt (Co), manganese (Mn), molybdenum (Mo), tungsten (W) and mixtures comprising at least one of the foregoing.

18. The catalyst composition according to claim 16, wherein M is present in an amount from 0.01 to 5 wt % based on the silico-zinc aluminate.

19. The catalyst composition according to claim 15, wherein the catalyst composition further comprises zinc aluminate and/or an oxide of silicon and/or an oxide of aluminum and/or an oxide of zinc.

* * * * *